United States Patent [19]

Yeung

[11] Patent Number: 4,576,918

[45] Date of Patent: Mar. 18, 1986

[54] METHOD OF SAMPLING AND ANALYZING BIOCIDAL GAS FROM A REACTION CHAMBER

[76] Inventor: Anthony C. Yeung, D4 Greenville Gardens 22/F, Shiu Fai Terrace, Hong Kong

[21] Appl. No.: 463,286

[22] Filed: Feb. 2, 1983

[51] Int. Cl.[4] .............................................. G01N 1/24
[52] U.S. Cl. ................................ 436/179; 73/864.52; 422/34; 422/103; 436/1; 436/93; 436/181
[58] Field of Search ..................... 436/179, 93, 181, 1; 422/83, 103, 102, 34; 73/864.52

[56] References Cited

U.S. PATENT DOCUMENTS

| | | | |
|---|---|---|---|
| 2,411,157 | 11/1946 | Fene et al. | 73/864.52 |
| 3,627,469 | 12/1971 | Cheng | 436/1 |
| 3,817,108 | 6/1974 | Principe et al. | 73/864.52 |
| 3,861,875 | 1/1975 | Joslyn | 422/62 X |
| 3,866,474 | 2/1975 | Hasselmann | 422/83 |
| 3,982,893 | 9/1976 | Joslyn | 422/3 X |
| 4,008,621 | 2/1977 | Ostojic et al. | 422/83 |
| 4,065,972 | 1/1978 | Holub et al. | 73/864.52 |
| 4,301,113 | 11/1981 | Alguire et al. | 422/2 |
| 4,336,721 | 6/1982 | Curtis | 204/431 X |
| 4,452,091 | 6/1984 | Richers | 73/864.52 |

*Primary Examiner*—David L. Lacey
*Assistant Examiner*—Robert J. Hill, Jr.
*Attorney, Agent, or Firm*—Michael G. Berkman

[57] ABSTRACT

A method and apparatus for determining the composition and the concentration of biocidal gas and other gases contained in a reaction chamber during processing of material contained in the chamber and exposed to the treating gas. A valved pre-evacuated gas-sampling vessel is positioned in the reaction chamber and, thereafter, opened by remote control to receive a gas sample representative of the gaseous atmosphere present in the chamber. The sampling vessel is then closed, removed from the treatment chamber, and connected to apparatus for analyzing the gas in the vessel. The qualitative and quantitative composition of the treating gas is thus determined.

4 Claims, 3 Drawing Figures

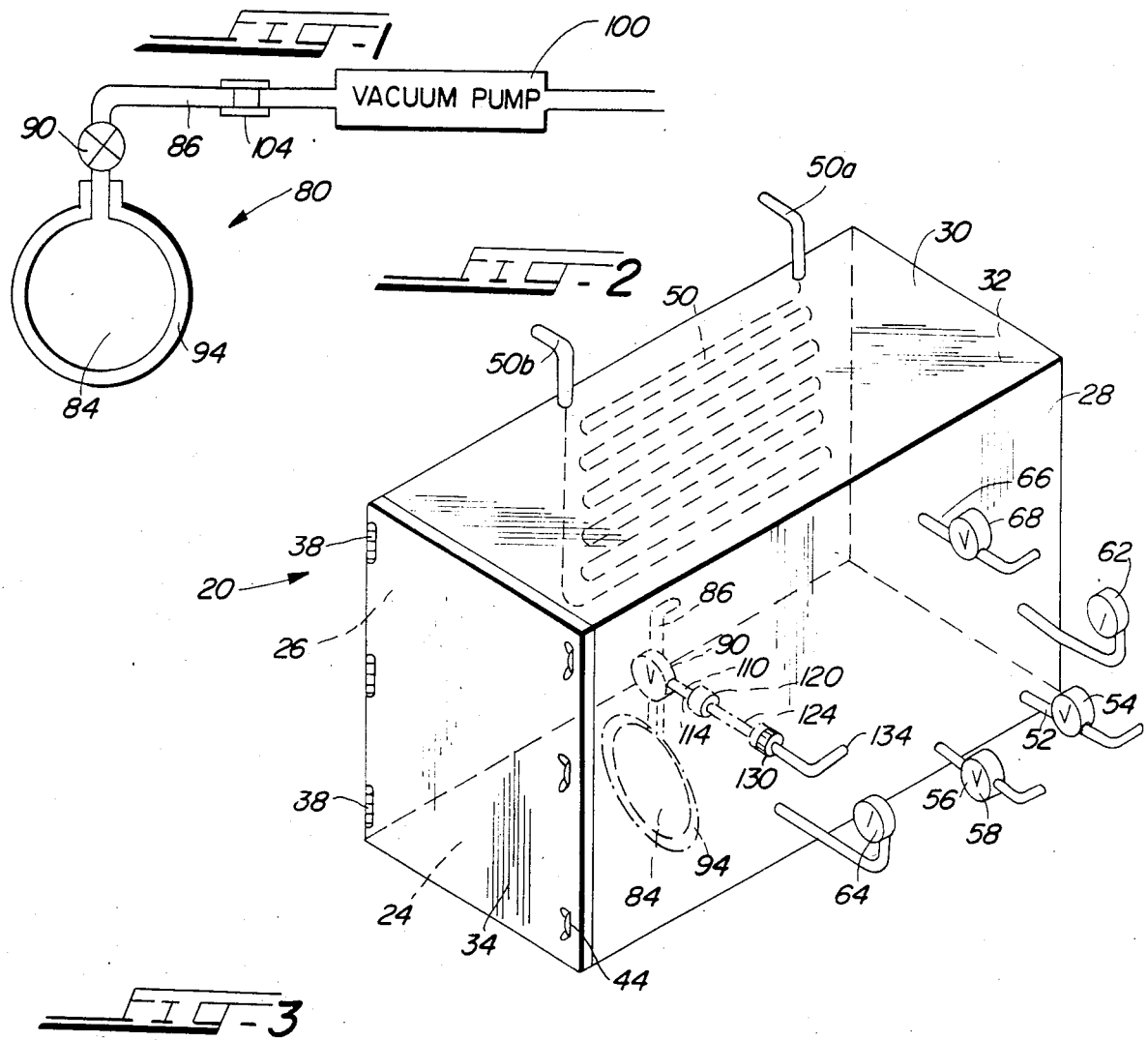

METHOD OF SAMPLING AND ANALYZING BIOCIDAL GAS FROM A REACTION CHAMBER

BACKGROUND OF THE INVENTION

The present invention relates to a technique and to apparatus for reliably sampling biocidal gas contained in a reaction chamber of the type used to treat, to deactivate or to destroy viable microorganisms and insects as well as lifecycle forms through which such organisms evolve. More particularly, the invention is directed to an apparatus and method by which the biocidal gas in the treating or reaction chamber is effectively sampled at any optionally selected predetermined time in the processing cycle.

The present invention finds special utility in processing systems in which the sterilant gas used is a mixture of an alkylene oxide such as ethylene oxide or propylene oxide with an inert diluent gas such as a halogenated hydrocarbon or carbon dioxide. The inert diluent is commonly used in such systems to eliminate flammability and to prevent the development of explosive atmospheres.

Gaseous systems of the type described are widely used in order to reduce the concentration of viable organisms in many types of products including food products and pharmaceutical products. The use of ethylene oxide as an active "sterilization" agent has proven an attractive technique because the gas itself is highly volatile and leaves essentially no residues. Nor is it destructive to the many types of materials which require treatment. A principal technique by which the actual sterilization treatment is conducted is to introduce the material to be treated into a relatively large chamber ($8' \times 8' \times 10'$) provided with suitable gas-tight doors, valving for introduction of sterilant gases, humidity control systems and heating tubes. The material having been introduced into the chamber, the latter is evacuated and then the sterilant gas mixture is introduced.

Typically, the gaseous mixture constitutes a mixture of ethylene oxide with a flourohydrocarbon such as trichloromonoflouromethane, dichlorodiflouromethane, and the like. The inherent flammability and potential explosiveness of ethylene oxide (in combination with air) is obviated through the incorporation of the inert flouro-chloro-hydrocarbon.

Since the effectiveness of the sterilization process using this type of gas mixture is dependent upon the proportional concentration of ethylene oxide in the gaseous mixture used, as well as the temperature and the exposure duration, it is most important to maintain accurate records of the concentration and composition of the sterilant gas mixture in the reaction chamber during the processing cycle. One technique has been to maintain a continuous monitoring of the gas composition by continuously sampling the gas in a flow system, the sampled gas being subjected to analysis using any preferred analytical techniques. However, in the continuous sampling procedure, the acquisition and transportation of the sample, while presenting component separation, has proved to be cumbersome and difficult. Additionally, the cost of the necessary "plumbing" has been high and there is a requirement that a highly trained technician be present at all times to carry out the necessary procedures. It is to the resolution and circumvention of these and other difficulties that the present invention is directed.

SUMMARY OF THE INVENTION

The present invention relates to a method and to apparatus whereby the biocidal gaseous mixture contained in the article treatment chamber may be effectively sampled on a "batch" basis. While this type of sampling has been attempted in the past, several problems have interfered with its successful practice. One of these is a difficulty in preserving the extracted sample and correlating the pressure and temperature of the sample with the values of these parameters existent during the sterilization process. Deviation from the temperature has been found responsible for the deposition (settling out) of components from the gaseous phase and, accordingly, inaccurate and unreliable analytical results.

The problems which have plagued the industry in prior art techniques have been effectively circumvented, in accordance with the practice of the present invention, by use of a special pre-evacuted sampling vessel. The vessel is positioned or located within the reaction or treatment chamber prior to carrying out the contemplated sterilization process. The evacuated vessel itself is provided with a suitable valve which can be actuated (opened and closed) from outside of the reaction chamber. Accordingly, at any desired time during the processing cycle, the valve to the pre-evacuated vessel is opened and, thereupon, a sample of the sterilant gas mixture is allowed to infiltrate or diffuse into and completely to fill the pre-evacuated vessel. The access valve to the vessel is then closed. After completion of the sterilization cycle, the now filled sampling vessel is retrieved, and the gaseous contents are analyzed.

In a preferred embodiment of the invention, the sampling vessel is provided with exterior insulation so that the equilibrium existent at the time of sampling, in the reaction chamber, is preferred within the sampler vessel itself, and the sample remains homogeneous.

It is a feature of the method of the invention that, optionally, one may use two or more sampling vessels so that representative samples of the gaseous mixture existing at any predetermined selectible stages of the processing cycle may be collected, for ultimate analysis.

At the completion of the sterilization cycle, and when the reaction chamber has been opened, the sample (or samples) vessel is connected into an analyzing system. Any preferred types of analyses may be conducted. These may include measurement of the ethylene oxide concentration, the moisture concentration and the concentration of the inert diluent gas.

In a preferred procedural technique constituting a facet of the invention, upon removal from the reaction chamber, connected or coupled to an auxiliary, second vessel which has also been previously evacuated. Preferably, the second vessel will have essentially the same volume as contained in the original pre-evacuated sampler. As a result of the technique described, it will be appreciated that the concentration of each gaseous component in the dual vessel system would be one-half of the concentation originally present in the reaction chamber at the time of sampling.

After the two interconnected sampling vessels have equilibrated in pressure and in the diffusion of the component gases, a sample of known volume (an "aliquot"), it withdrawn from the vessel assembly and introduced into an analyzer. The analyzer itself may utilize any preferred analytical techniques and procedures including gas chromotography techniques, infrared spectra measurement procedures, mass spectrometry, or nuclear magnetic resonance (NMR) techniques.

In addition to the option of using a plurality of pre-evacuated vessels in the reaction chamber, it will be understood that under conditions in which the treatment chamber is operated under a "negative" pressure, the contents transferred into the sampler vessel may ultimately be removed or withdrawn through the use of an auxiliary, inert gas such as dry air, helium, or nitrogen as a "pushing" medium.

It is an important feature of the apparatus and technique of the invention that the use of a well-insulated, pre-evacuated sampler in which the gaseous sample is collected for ultimate analysis is maintained in a state such that the pressure and temperature equilibria are perpetuated from the time of introduction of the sample, to the time of delivery to the analytical system, and are unchanged. It is an important practical advantage of the apparatus of the invention that it may be readily adapted for use with existing industrial equipment without any need for major modifications of that equipment.

A related advantage of the apparatus and technique of the invention is that the method of analysis which is ultimately invoked may be a method which has already been established as reliable and practical.

Other and further objects, advantages, and features of the invention will become apparent from a consideration of the specifications in conjunction with the drawings.

DESCRIPTION OF THE DRAWING

FIG. 1 illustrates diagramatically a gas sampling vessel, according to the invention, coupled to a vacuum pump for evacuating the vessel prior to its functional placement in a treatment chamber;

FIG. 2 is a schematic representation of a treatment chamber with the varied gas sampling vessel in a place inside, and with valve-controlling linkage coupled through the wall of the chamber to the outside, for remote manipulation; and FIG. 3 is a diagramatic representation of a gas sampling vessel according to the invention and connected into a gas analysis system.

DESCRIPTION OF PREFERRED EMBODIMENT

The aims, objects, and advantages of the invention are achieved by the introduction, into a biocidal gas containing chamber, a pre-evacuated gas sampling vessel, and coupling the control valve of that gas sampling vessel, through the chamber wall, for access and manipulation exteriorly of the chamber itself. Preferably, the gas sampling vessel is insulated or "lagged" to preserve, within the sampling vessel, the same equilibria conditions existent at the time the gas was sampled. Finally, the sample-containing vessel is connected functionally to a gas analyzer so that the composition of the sampled gas may be determined both qualitatively and quantitatively. Still others of the aims and advantages of the invention are achieved by carrying out an initial controlled reduction in the concentration of the gas to be analyzed, this being achieved by intercoupling the gas-filled sample vessel to a second, previously evacuated auxiliary vessel. Preferably, the auxiliary, second vessel has the same internal volume as the original sampling vessel.

Referring now to the drawings, and particularly to FIG. 2, there is shown, for illustrative purposes and not in any limiting sense, a treatment or reaction chamber 20 of the general type in which the sampling vessel and method of the present invention find utility. As shown, the chamber 20 is a generally elongated box-like configuration having a floor 24, a pair of opposed side walls 26 and 28, a top 30, a rear end wall 32 and a front wall 34. In the specific embodiment of the vessel 20 illustrated, the front wall 34 is provided with a plurality of lateral hinges 38 pivotally supporting the front wall 34 so that the latter acts as a closure door and may be swung to a fully opened position.

At its lateral end opposite the hinges 38, the front wall 34 is provided with vertically spaced door-securement mechanisms 44. The chamber is constructed of relatively heavy gauge steel, and the walls themselves may be further stiffened and strengthened by means of channels, H-bars or similar reinforcements so that the chamber may be used either as a vacuum chamber or in hyperbaric applications.

Further to ensure the versatility of the reaction chamber 20, the latter is provided with auxiliary structures including heater means which, in the specific illustrated apparatus comprise convuluted or sinuously disposed steam coils 50 provided with input and exhaust leads 50a and 50b, supported on the interior face of the side wall 26 of the chamber 20. The treatment vessel 20 is also provided with means for introducing various utilities, for example, a water or water vapor input line 52 and a control valve 54, a pipe 56 for introduction and withdrawal of sterilant gas, and a control valve 58, a pressure sensor and indicator 62, and a thermometer 64. Additionally, the chamber is fitted with a pipe 66 and control valve 68 which may be used for evacuating the chamber 20 itself.

The above-described reaction chamber is of a type known in the prior art and is, per se, not an element of the present invention. Rather, it constitutes a type of system in which the present invention finds utility. Specifically, the subject invention is directed to a simple yet highly effective method and associated apparatus whereby one may obtain a reliably representative sample of the gaseous environment present in the sterilization or the reaction chamber 20 at any preferred selectable period or over a series of time-spaced periods.

Referring further to FIG. 1, a novel gas sampling assembly 80, in accordance with the invention, is shown as comprising, in a preferred embodiment, a vessel 84, of any practical volume, but preferably having a volume in the range of from about 1 to about 2 liters. The vessel 84 is fitted with a lead line or conduit 86 and a valve or closure mechanism 90. Enveloping the vessel 84 itself is an insulation layer or lagging material 94 disposed as an enveloping jacket.

In carrying out the method of the invention, the sampling assembly 80 is connected to a vacuum pump 100 (FIG. 1) by means of a coupler 104, whereby the sample vessel 84 is evacuated to a relatively high degree, preferably to a pressure of less than about 5 mm of mercury, and the valve 90 closed. The sampling assembly 80 is then introduced into the reaction chamber 20. A valve actuating rod or bar 110 is connected to the valve 90 and the other end 114 of the valve control bar 110 is attached by means of a coupler 120 to an elongated rod 124 which passes through a wall-mounted fluid-tight bushing 130 to the exterior of the reaction vessel 20. At its outwardly projecting limit, the bar 124 terminates in a handle 134 by means of which the valve 90 may be controlled from the exterior of the reaction vessel 20.

The gas sampling assembly 80 of the invention is used without interfering with the normal operation of the sterilization or treatment chamber 20. That is, with the sampling vessel 84 in place as described above, the elected "sterilization" process is carried out in the usual manner. At a selectable time during the processing routine or cycle, the gaseous environment then existing in or pervading the reaction chamber 20 is "sampled" by opening the valve 90, remotely, by means of the exterior control handle 134 and its associated linkage 124, 120 and 114. After the sampling vessel 84 has equilibrated with the gaseous environment in the reaction vessel 20, the valve 90 is closed. At this instant, the gaseous composition captured and secured in the sampling vessel 84 conforms in all substantive respects to the gas present in the reaction vessel.

Upon completion of the sterilization cycle, or at any other time selected, the gas sampling assembly 80 is removed from the chamber 20. Optionally, the assembly 80 may then be coupled directly to a gas analyzer 140, and the gaseous contents and composition of the sampling vessel 84 determined.

In a preferred embodiment of the invention, a somewhat more sophisticated technique is adopted. The vessel 84, containing the gaseous sample, is connected through a conduit 144 and a coupler 146 to the gas analyzer 140. A second vessel 150 which has previously been evacuated is also connected by means of a coupler 154, a conduit 156 and a connector 160 to the gas analyzer 140, so that the two vessels 84 and 150 are connected in series, as shown in FIG. 3. As in the case of the sampling assembly 80, the second gas sampling vessel 150 is fitted with a closure or a control valve 164.

Two arms of a T or yoke 166 connect the vessels 84 and 150 to a vacuum pump 100 through a valve 170 and a connector 174. As shown, the third arm of the T 166 connects the assembly to the gas analyzer 140.

As indicated diagramatically in FIG. 3, if preferred, the T or yoke assembly with the two vessels 84 and 150 may be housed in an environmentally-controlled container or box 180, the temperature of which may be controlled. For example, the temperature may be reset to the temperature existent at the time the sample of gas was taken in the reaction chamber 20.

With the sample vessels 84 and 150 connected as illustrated, valve 170 is opened, whereupon the vacuum pump 100 is actuated and the lead lines evacuated up to the vessel shut-off valves 90 and 164. The valve 170 is then closed and the valves 90 and 164 are opened so that the gas contained in the sampling vessel 84 may distribute and equilibrate, in the system with the second vessel 150, and flow through a sampling loop 186 in the gas analyzer 140. Preferably, the valving is carefully controlled and the flow rate restricted so as to minimize the cooling effect normally accompanying the expansion of a gas as it leaves a "pressurized" container.

A sample of the gas, in known volume, is introduced into the gas analyzer 140 at the injection loop 186, in the conventional manner. From the data provided by the gas analyzer, one may readily determine the composition of, and may also calculate the concentration of the gaseous components contained in the original sample vessel 80, utilizing the ideal gas laws. It will be appreciated that for simplicity, it is convenient to use as the second vessel 150 a container which has essentially the same volume as that of the sampling vessel 84. Under such conditions, the gas which is ultimately delivered into the analyzer is at a concentration which is essentially one-half of what was present in the reaction chamber 20 at the time the sample was taken.

To facilitate qualitative identification of the sterilant gas composition, it may be necessary continuously to feed the gas sample into the gas analyzing device 140, such a device being, optionally, a mass spectrometer. Under such conditions, and if the sterilizing chamber 20 had originally been under a "negative" pressure, the gaseous contents in the sampling vessel 84 may conveniently be "pushed out" of the sampler into the analyzer through the use of an inert gas such as dry air, nitrogen or helium.

While preferred embodiments of the invention have been illustrated and described, other variations may be made utilizing the inventive concept herein disclosed. For example, two or more separate gas sampling vessels may be introduced into the reaction chamber prior to carrying out a particular sterilization process. These sampling vessels may be used for obtaining samples at various spaced locations in the reaction vessel 20, and/or may be used to sample the gaseous contents of the reaction vessel at selectible time-spaced intervals. While the precise type of gas analyzing device is not critical in the practice of the present invention, it is contemplated that such analytical techniques as gas chromatography, mass spectrometry, and nuclear magnetic resonance (NMR) may be utilized. The use of insulation blankets or wrapping for the sampling vessel enables the gas analysis to be carried out without any disruption of the temperature conditions existent at the time the sample gas was introduced into the sampling vessel. The refinements described enable one to avoid phase separation and to ensure uniformity in the gaseous aliquot subjected to analysis.

It is intended that all of the above-described variations and others which may become apparent to those skilled in the art upon reading the present disclosure be considered as within the scope of the invention as defined in the following claims.

What is claimed is:

1. A method of determining the composition and concentration of a biocidal gas present in a reaction chamber during processing of material contained in the chamber and exposed to the biocidal gas, said method comprising the steps of covering a valved, fixed-volume, reuseable gas sampling vessel having an interior with an enveloping jacket as an insulating layer therefor, evacuating said vessel, placing the evacuated vessel within a reaction chamber containing articles to be processed, providing a remotely operable valve control means accessible outside of the reaction chamber, coupling said remotely operable valve control means to the valve of said sampling vessel in the reaction chamber for selectively manipulating the valve, closing the reaction chamber and introducing article-treating biocidal gas thereinto for processing material contained in the chamber, establishing gaseous flow communication between the interior of said evacuated sampling vessel and the reaction chamber by manipulating the valve of said valved vessel through said remotely operable valve control means to open the valve, holding the valve in an open position for a finite time period sufficient to allow a gaseous atmosphere present in the reaction chamber to diffuse into and to fill said sampling vessel and to establish equilibrium between gases in said sampling vessel and in said chamber, closing the valve of said valved gas sampling vessel to trap and to seal therewithin an aliquot of the gaseous atmosphere present in said reaction chamber, retrieving the gas-filled sampling vessel from said reaction chamber, and analyzing the gas contained in said vessel.

2. The method as set forth in claim 1 further comprising reducing the concentration of gas in said sampling vessel by a selectable known volume ratio prior to analyzing the gas, and wherein reduction of the concentration of gas contained in said sampling vessel includes a step of intercoupling said gas containing sampling vessel with an evacuated second vessel, establishing unrestricted intercommunicating flow between said gas sampling vessel and the second evacuated vessel, thereby providing a homogeneous equilibrium system having a selectable, known reduced concentration of gases, and removing an aliquot of gas from the equilibrium system for analysis.

3. The method as set forth in claim 2 wherein said second vessel has a volume essentially the same as that of said gas sampling vessel.

4. The method as set forth in claim 3 wherein each of said gas sampling vessel and said second vessel have a volume in a range of from about 1 to about 2 liters.

* * * * *